US008568768B2

(12) United States Patent
Reneker et al.

(10) Patent No.: US 8,568,768 B2
(45) Date of Patent: Oct. 29, 2013

(54) SEQUESTERED REACTIVE MATERIALS

(75) Inventors: Darrell H. Reneker, Akron, OH (US); Daniel J. Smith, Stow, OH (US)

(73) Assignee: The University of Akron, Akron, OH (US)

( * ) Notice: Subject to any disclaimer, the term of this patent is extended or adjusted under 35 U.S.C. 154(b) by 1281 days.

(21) Appl. No.: 10/554,191

(22) PCT Filed: Apr. 23, 2004

(86) PCT No.: PCT/US2004/012673
§ 371 (c)(1),
(2), (4) Date: Aug. 3, 2006

(87) PCT Pub. No.: WO2004/094050
PCT Pub. Date: Nov. 4, 2004

(65) Prior Publication Data
US 2006/0280781 A1    Dec. 14, 2006

Related U.S. Application Data

(60) Provisional application No. 60/464,879, filed on Apr. 23, 2003.

(51) Int. Cl.
*A61K 9/70*      (2006.01)
*A61F 13/00*     (2006.01)
*B32B 5/02*      (2006.01)

(52) U.S. Cl.
USPC .......................................... 424/443; 442/123

(58) Field of Classification Search
USPC ........................................................ 424/443
See application file for complete search history.

(56) References Cited

U.S. PATENT DOCUMENTS

| | | | |
|---|---|---|---|
| 3,991,766 A | 11/1976 | Schmitt et al. | |
| 5,405,919 A | 4/1995 | Keefer et al. | |
| 5,545,409 A | 8/1996 | Laurencin et al. | |
| 5,650,447 A | 7/1997 | Keefer et al. | |
| 5,798,115 A * | 8/1998 | Santerre et al. | 424/423 |
| 5,994,444 A | 11/1999 | Trescony et al. | |
| 6,103,275 A | 8/2000 | Seitz et al. | |
| 6,190,704 B1 | 2/2001 | Murrell | |
| 6,232,434 B1 * | 5/2001 | Stamler et al. | 528/373 |
| 6,685,956 B2 | 2/2004 | Chu et al. | |
| 6,689,374 B2 | 2/2004 | Chu et al. | |
| 6,706,274 B2 * | 3/2004 | Herrmann et al. | 424/423 |
| 6,709,681 B2 | 3/2004 | Benjamin et al. | |
| 2002/0155164 A1 | 10/2002 | Figley et al. | |
| 2003/0165578 A1 | 9/2003 | Murrell | |
| 2004/0009238 A1 | 1/2004 | Miller et al. | |
| 2004/0018226 A1 | 1/2004 | Wnek et al. | |
| 2004/0076661 A1 | 4/2004 | Chu et al. | |

FOREIGN PATENT DOCUMENTS

| | | | |
|---|---|---|---|
| EP | 0 752 866 | 1/1997 | |
| WO | WO 99/18949 | 4/1999 | |
| WO | 01/26792 A2 | 4/2001 | |
| WO | WO 01/26610 | 4/2001 | |
| WO | WO 01/26702 | 4/2001 | |
| WO | WO 01/89572 | 11/2001 | |
| WO | WO 01/89572 A1 * | 11/2001 | 424/401 |
| WO | WO 02/00149 * | 1/2002 | 424/401 |
| WO | 02/20026 A2 | 3/2002 | |
| WO | 02/094985 A2 | 11/2002 | |
| WO | WO 03/086290 | 10/2003 | |

OTHER PUBLICATIONS

Anand, Vikas; Kandarapu, Raghupathi; and Garg, Sanjay. Ion-exchange resins: carrying drug delivery forward. DDT vol. 6, No. 17, Sep. 2001, pp. 905-914.*
Indian Office Action in Indian Patent Application No. 5060/DELNP/2005 dated May 23, 2008.
Chinese Office Action in Chinese Patent Application No. 200480017111.8 dated Feb. 6, 2009.
Australian Office Action in Australian Patent Application No. 2004233347 dated May 13, 2009.

* cited by examiner

*Primary Examiner* — Fereydoun G Sajjadi
*Assistant Examiner* — Audrea Buckley
(74) *Attorney, Agent, or Firm* — Renner Kenner Greive Bobak Taylor Weber

(57) ABSTRACT

A fibrous assembly is provided for performing site-specific chemistry. In general the present invention provides a fibrous assembly comprising a first fiber that sequesters a first reactive component; and a second fiber that sequesters a second reactive component, wherein at least the first or second fiber releases its reactive component when the fiber is in the presence of a releasing agent, and wherein when the at least first or second fiber releases its reactive component, the first and second reactive components react with each other to form a reaction product. Related methods of manufacture and use are also provided.

34 Claims, No Drawings

SEQUESTERED REACTIVE MATERIALS

This patent application claims priority to U.S. Provisional Application Ser. No. 60/464,879 that was filed on Apr. 23, 2003.

FIELD OF THE INVENTION

This invention relates to fibrous assemblies that sequester reactive components. The invention is further directed to fibrous assemblies that can be used to deliver reactive components to targeted locations. Still further, this invention is directed to fibrous assemblies that can be used in performing chemistry at specific locations.

BACKGROUND OF THE INVENTION

There is a well-known need for performing site-specific chemistry.

Site-specific chemistry is useful in a number of applications wherein a reaction product cannot be readily delivered to a targeted location. A nonlimiting example of such a reaction product is a gaseous-phase composition. Nitric oxide is a specific example. In order to introduce a gaseous-phase composition to a target location, a reaction that produces the gaseous-phase reaction product can be performed at the target location. Therefore, the art needs a composition or method that can deliver reactive components to the target location in proximity to each other so that the reactive components can come into contact and react to thereby form a reaction product.

SUMMARY OF THE INVENTION

In general the present invention provides a fibrous assembly comprising a first fiber that sequesters a first reactive component; and a second fiber that sequesters a second reactive component, wherein at least the first or second fiber releases its reactive component when the fiber is in the presence of a releasing agent, and wherein when the at least first or second fiber releases its reactive component, the first and second reactive components react with each other to form a reaction product.

The present invention also provides a method for preparing a fibrous assembly comprising the steps preparing a first fiber that sequesters a first reactive component; preparing a second fiber that sequesters a second reactive component; and incorporating the first and second fiber into a fibrous assembly, wherein at least the first or second fiber releases its sequestered reactive component when that fiber is exposed to a releasing agent, and wherein when at least the first or second sequestered reactive component is released from its respective fiber, the first and second reactive components react with each other to form a reaction product.

The present invention further provides a medical-treatment method comprising the step treating a patient with a fibrous assembly, wherein the fibrous assembly has a first fiber that sequesters a first reactive component; and a second fiber that sequesters a second reactive component, wherein at least the first or second fiber releases its reactive component when that fiber is exposed to a releasing agent, and wherein when at least the first or second reactive component is released from its respective fiber, the first and second reactive components react to form a reaction product.

The present invention further provides a method for creating an epoxy-type adhesive comprising the step adding a releasing agent to a fibrous assembly having a first fiber that sequesters a urethane prepolymer and second fiber that sequesters a diamine, wherein at least the urethane prepolymer or the diamine is released from its fiber when that fiber is in the presence of the releasing agent, and wherein when at least the urethane prepolymer or the diamine is released from its respective fiber, the urethane prepolymer and diamine react with each other to form an epoxy-type adhesive.

The present invention further provides a fibrous assembly comprising a first fiber that sequesters a first reactive component, wherein when the first reactive component is in the presence of a releasing agent, the first reactive component reacts with the releasing agent to produce a reaction product.

DETAILED DESCRIPTION OF ILLUSTRATIVE EMBODIMENTS

This invention is generally directed to compositions and methods that relate to a fiber that sequesters a reactive component and then releases the reactive component when the fiber is exposed to a releasing agent.

This invention is more specifically directed to compositions that are constructed with at least one fiber that sequesters and then proceeds to release a reactive component when the fiber is exposed to a releasing agent. Once released from the fiber, the reactive component preferably reacts with another reactive component to form a reaction product that is preferably tailored to a particular application.

The invention is further directed to compositions constructed with two or more fibers that sequester and then release reactive components when at least one of the fibers is exposed to a releasing agent. More specifically, the first fiber sequesters and can release a first type of reactive component, and the second fiber sequesters and can release a second type of reactive component. Preferably, when the two fibers are exposed to a releasing agent(s), both types of reactive components are released from their respective fibers and preferably go on to react with one another to form a reaction product that is tailored to a particular application.

A reactive component is sequestered by a fiber when the reactive component is mechanically bound within the fiber, chemically bonded to the fiber, otherwise attached to the fiber, or combinations thereof. Being mechanically bound within a fiber means that the reactive component is physically restrained or tethered within the fiber. And this understanding contemplates that the reactive component may not be completely encapsulated within the fiber and that a portion of the reactive component may be exposed at the fiber surface.

Simply put, a reactive component is chemically bound to a fiber if there is a chemical bond that attaches the reactive component to the fiber.

This invention's fibers are not limited by any characteristic dimension or any method of preparation. For example, the fibers are not limited to any particular diameter, length, denier, or other physical characteristic. But preferably, the fibers are nanofibers, and more preferably they are electrospun nanofibers. Alternate methods of preparation can also be used to manufacture the fibers—one such method prepares the nanofibers by gas-jet methods (NGJ). NGJ methods are well known to persons of ordinary skill in the art.

When sequestered by a fiber, the useful physical form of a sequestered reactive component is not limited to any particular form. On the contrary, a sequestered reactive component can take a variety of physical forms. Nonlimiting examples of useful physical forms of sequestered reactive components are: a particle, a dissolved molecule, a fibrous skeleton created by electrospinning, a uniform coating on the surface of the fiber, a ribbon, a tube, a gas-filled pore, a fluid-filled pore, or a compound chemically bound to an ion-exchange-resin bead, or a combination thereof.

When sequestered in the form of a fluid-filled pore, nonlimiting examples of the fluid are a wax, oil, oligomer-containing fluid, low-molecular-weight liquid, or combination thereof.

Nonlimiting examples of reactive components that can be sequestered by a fiber include: a carboxylic acid, an ascorbic acid, potassium nitrite, a nitrite, a urethane prepolymer, a diamine, and a diol.

There are no upper or lower limits on either the number or concentration of reactive components that can be sequestered by a single fiber.

There is no limitation on the different types of reactive components that can be sequestered by a single fiber. In fact, any reactive component that can be sequestered by a fiber can be used in this invention. There is additionally no limit on the number of different types of reactants that can be sequestered by a single fiber. In one embodiment, one type of reactive component is sequestered by a single fiber. In another embodiment, there are two or more distinct reactive components that are sequestered by a single fiber.

Anything that, when exposed to a subject fiber, triggers the release of a reactive component from the subject fiber is useful as a releasing agent. There is no limitation on what can be used as a releasing agent. Nonlimiting examples of useful releasing agents are: a solvent, a signaling substance, radiation, heat, a mechanical force, a charged particle, an electron, a magnetic particle, a magnetic field, forces from a flowing fluid, hydrostatic pressure, mechanical deformation, or a combination thereof.

There is no limit on the methods that can be employed in preparing fibers that sequester a reactive component or substances. Reactive components can become sequestered by a fiber either during or after the fiber manufacturing process. As a nonlimiting example of sequestering a reactive component during the fiber's manufacturing process, one exemplary method sequesters a reactive component directly into a fiber during an electrospinning process. This is achieved by adding the reactive component(s) directly to an electrospinnable solution and then electrospinning that solution. During the electrospinning process, the reactive component becomes sequestered into the fiber. Electrospinning and its parameters are well known, and a person of ordinary skill in the art will be able to sequester a reactive component into a fiber via electrospinning methods without having to perform undue experimentation.

The concentration of reactive components within an electrospinnable solution is in no way limited by an upper or lower limit. Useful concentrations can easily be determined by persons of ordinary skill in the art without having to perform undue experimentation. The desired concentration of reactive components that are to be sequestered by a fiber will help to determine the concentration of reactive components that need to be present in an electrospinnable solution. And the electrospinnable-solution concentrations can easily be determined.

In another embodiment, reactive components are sequestered into a fiber during fiber manufacture by a nanofiber-by-gas-jet (NGJ) method. This is achieved by adding the reactive component to the fluid mixture that is to be used in the NGJ method. NGJ methods are well known, and a person of ordinary skill in the art will be able to prepare NGJ fibers having sequestered reactive components therein without having to perform undue experimentation.

The concentration of reactive components within the NGJ fluid mixture is in no way limited by an upper or lower limit.

Useful concentrations can easily be determined by persons of ordinary skill in the art without having to perform undue experimentation. The desired concentration of reactive components that are to be sequestered by a fiber will help to determine the concentration of reactive components that need to be present in an NGJ fluid mixture. And the NGJ fluid mixture concentrations can easily be determined.

This invention's fibrous assemblies typically have at least two distinct fibers that each sequester reactive components. More specifically, a first fiber sequesters and can release at least a first type of reactive component, and a second fiber sequesters and can release at least a second type of reactive component. When both of the fibers are exposed to a releasing agent(s), both the first and second type of reactive components are released from their respective fiber and preferably proceed to react with each other. The fibrous assemblies are therefore well suited for delivering chemically reactive components to a targeted location. Further, a fiber's release of reactants is regulated by the timing of the fiber's exposure to a releasing agent.

Within one embodiment of a fibrous assembly, the first and second distinct fibers are preferably positioned proximate to each other so that when the fibers release their reactive components, the reactive components can react with each other. In order to position the at least two distinct fibers proximate to each other, the fibers are preferably woven together or at least placed in contact with one another at at least one location on each fiber. And there is no limitation on the different fiber constructions that can be employed in this invention. A nonlimiting example of a preferred embodiment for positioning the fibers proximate to each other is to contact a nonwoven mat of a first fiber with a nonwoven mat of a second fiber. More preferably, the two nonwoven mats are in contact and overlap.

In another embodiment, a fibrous assembly has at least a first fiber that sequesters a first reactive component. And when the first reactive component is in the presence of a releasing agent, the first reactive component reacts with the releasing agent to produce a reaction product. The releasing agent can also serve the purpose of releasing the first reactive component from the first fiber. In this particular embodiment, a second fiber is not required to be part of the fibrous assembly, and a chemical reaction occurs between the releasing agent and first reactive component. Further, within this embodiment, the fiber can be manufactured entirely from the first reactive component.

The fibrous assemblies are useful for delivering reactive components to targeted locations and as a result, there is no limit on how the assemblies can be used. A preferred use for a fibrous assembly is a nitric-oxide releasing medical dressing directed to treating wounds and other lesions of the skin—such as warts. In another embodiment, the fibrous assembly is useful is creating epoxy-type adhesives.

In order to demonstrate the practice of the present invention, the following examples have been prepared and tested. The examples should not, however, be viewed as limiting the scope of the invention. The claims will serve to define the invention.

EXAMPLES

Specific Examples

A nanofiber assembly contains at least two types of fibers, each sequestering a reactive component. In this example, fiber one contains ascorbic acid; fiber two contains potassium nitrite. Ascorbic acid and potassium nitrite may or may not be soluble in the polymer solution prior to electrospinning. Fiber polymers may or may not dissolve in water. Fiber mat formed above, when exposed to moisture, releases ingredients to give ascorbic acid and $NO_2-$, which react to form nitric oxide (NO). Alternatively, nitrate and/or ascorbic acid may be immobilized such as by being adsorbed onto an ion exchange resin bead, which is then incorporated into polymer fibers or nanofibers. One or more of the bead-bound reactive compounds, will therefore not leach from the fibers on exposure to moisture, but will only react in situ on the bead. For example, ascorbic acid may be incorporated into a first nanofiber and ion exchange resin bead-bound nitrite may be incorporated into a second nanofiber. Neither component will leach from the fibers in the absence of moisture. However, on exposure to a solvent for the polymer of the first fiber, or another compound which allows release of ascorbic acid from the first fiber, the ascorbic acid will be released and react with the bound nitrite, releasing nitric oxide. Intervening layers of fibers may also be incorporated to regulate the migration of ascorbic acid to the nitrite containing fibers.

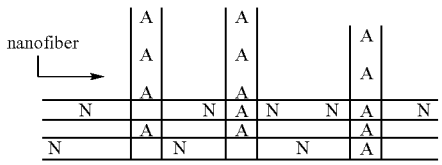

A = Ascorbic Acid
N = K + $NO_2^-$ (nitrite)

In another example, one type of fiber contains a urethane prepolymer, while a second fiber contains a crosslinker as shown schematically below.

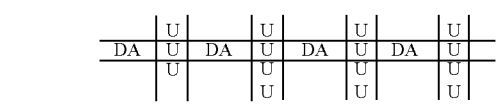

U = urethane prepolymer (Hypol™)
DA = diamine (crosslinker)

No reaction will occur until the nanofibers dissolve or swell in solvent.

Fiber assemblies as described above are envisioned as being use in nitric oxide-releasing medical dressings for the treatment of wounds and other lesions of the skin such as warts. This method may also be useful in other fields where the sequestration of reactive component is desired, such as in the creation of epoxy-type adhesives.

Various modifications and alterations that do not depart from the scope and spirit of this invention will become apparent to those skilled in the art. This invention is not to be duly limited to the illustrative embodiments set forth herein.

What is claimed is:

1. A fibrous assembly comprising:
   a first nanofiber that sequesters a first reactive component; and
   a second nanofiber that sequesters a second reactive component,
   wherein at least the first and second nanofiber release their reactive components when the nanofibers are in the presence of a releasing agent, and
   wherein when the at least first and second nanofibers release their reactive components, the first and second reactive components react with each other to form a reaction product.

2. The fibrous assembly of claim 1, wherein at least the first or second nanofiber is polymeric.

3. The fibrous assembly of claim 1, wherein at least the first or second reactive component is a particle, a dissolved molecule, a fibrous skeleton that was created by electrospinning, a uniform coating, a ribbon, a tube, a gas-filled pore, a fluid-filled pore, or bound to an ion-exchange-resin bead.

4. The fibrous assembly of claim 1, wherein the reaction product of the first reactive component and the second reactive component is nitric oxide.

5. The fibrous assembly of claim 1, wherein the first reactive component is a carboxylic acid and the second reactive component is nitrite.

6. The fibrous assembly of claim 1, wherein the first reactive component is a urethane prepolymer and the second reactive component is a diamine or diol.

7. The fibrous assembly of claim 1, wherein at least the first or second reactive component is bound to an ion-exchange-resin bead.

8. The fibrous assembly of claim 1, wherein the releasing agent is a solvent, a signaling substance, radiation, heat, a mechanical force, a charged particle, an electron, a magnetic particle, a magnetic field, forces from a flowing fluid, hydrostatic pressure, mechanical deformation, or a combination thereof.

9. The fibrous assembly of claim 1, wherein the releasing agent is a solvent.

10. The fibrous assembly of claim 1, wherein at least the first or second nanofiber dissolves or swells in the presence of the releasing agent.

11. The fibrous assembly of claim 3, wherein the fluid is a wax, oil, oligomer-containing fluid, low-molecular-weight liquid, or combination thereof.

12. The fibrous assembly of claim 5, wherein the carboxylic acid is ascorbic acid.

13. A method for preparing a fibrous assembly comprising the steps:
    preparing a first nanofiber that sequesters a first reactive component;
    preparing a second nanofiber that sequesters a second reactive component; and
    wherein at least the first and second nanofibers release their sequestered reactive components when the nanofibers are exposed to a releasing agent, and
    wherein when at least the first and second sequestered reactive components are released from its respective nanofiber, the first and second reactive components react with each other to form a reaction product.

14. The method of claim 13, wherein the first nanofiber is prepared by electrospinning a first electrospinnable solution having a first polymer and a first reactive component; and
    wherein the second nanofiber is prepared by electrospinning a second electrospinnable solution having a second polymer and a second reactive component, wherein the second reactive component is reactable with the first reactive component.

15. The method of claim 13, wherein a reaction product of the first reactive component and the second reactive component is nitric oxide.

16. The method of claim 13, wherein the first reactive component is a carboxylic acid and the second reactive component is nitrite.

17. The method of claim 13, wherein the first reactive component is a urethane prepolymer and the second reactive component is a diamine or diol.

18. The method of claim 13, wherein at least the first or second reactive component is bound to an ion-exchange-resin bead.

19. The method of claim 13, wherein at least the first or second reactive component is a particle, a dissolved molecule, a fibrous skeleton that was created by electrospinning, a uniform coating, a ribbon, a tube, a gas-filled pre, a fluid-filled pore, or bount to an ion-exchange-resin bead.

20. The method of claim 14, wherein electrospinning the first electrospinnable solution results in a first nanofiber that sequesters the first reactive component, and wherein electrospinning the second electrospinnable solution results in a second nanofiber that sequesters the second.

21. The method of claim 16, wherein the carboxylic acid is ascorbic acid.

22. The method of claim 19, wherein the fluid is a wax, oil, oligomer-containing fluid, low-molecular-weight liquid, or combination thereof.

23. A fibrous assembly comprising:
a first nanofiber that sequesters a first reactive component, wherein the first nanofiber releases its reactive component when the nanofiber is in the presence of a releasing agent and the reactive component and the releasing agent react to produce a reaction product.

24. The fibrous assembly of claim 23, wherein the first nanofiber is polymeric.

25. The fibrous assembly of claim 23, wherein at least the first reactive component is a particle, a dissolved molecule, a fibrous skeleton that was created by electrospinning, a uniform coating, a ribbon, a tube, a gas-filled pore, a fluid-filled pre, or bound to an ion-exchange-resin bead.

26. The fibrous assembly of claim 23, wherein the reaction product of the first reactive component and the releasing agent is nitric oxide.

27. The fibrous assembly of claim 23, wherein the first reactive component is a carboxylic acid or nitrite.

28. The fibrous assembly of claim 23, wherein the first reactive component is a urethane prepolymer, a diamine, or a diol.

29. The fibrous assembly of claim 23, wherein at least the first reactive component is bound to an ion-exchange-resin bead.

30. The fibrous assembly of claim 23, wherein the releasing agent is a solvent, a signaling substance, radiation, heat, a mechanical force, a charged particle, an electron, a magnetic particle, a magnetic field, forces from a flowing fluid, hydrostatic pressure, mechanical deformation, or a combination thereof.

31. The fibrous assembly of claim 23, wherein the releasing agent is a solvent.

32. The fibrous assembly of claim 23, wherein the first nanofiber dissolves or swells in the presence of the releasing agent.

33. The fibrous assembly of claim 25, wherein the fluid is a wax, oil, oligomer-containing fluid, low-molecular-weight liquid, or combination thereof.

34. The fibrous assembly of claim 27, wherein the carboxylic acid is ascorbic acid.

* * * * *